United States Patent [19]

Kyo et al.

[11] 4,381,416
[45] Apr. 26, 1983

[54] PROCESS FOR PRODUCING ISOPRENE

[75] Inventors: Sunao Kyo; Tumoru Renge; Katsumi Omura, all of Hasaki, Japan

[73] Assignee: Kuraray Co., Ltd., Okayama, Japan

[21] Appl. No.: 211,712

[22] Filed: Dec. 1, 1980

[30] Foreign Application Priority Data

Dec. 4, 1979 [JP] Japan .................................. 54-157866

[51] Int. Cl.$^3$ .......................... C07C 1/24; C07C 11/18
[52] U.S. Cl. ..................................... 585/606; 585/607; 585/609; 585/610; 585/639; 585/640
[58] Field of Search ............... 585/606, 609, 610, 639, 585/640, 607

[56] References Cited

U.S. PATENT DOCUMENTS

| | | | |
|---|---|---|---|
| 2,502,431 | 4/1950 | Copenhaver et al. | 585/607 |
| 3,105,857 | 10/1963 | Ackermann | 585/607 |
| 3,284,533 | 11/1966 | Mitsutani | 585/607 |
| 3,793,390 | 2/1974 | Takagi et al. | 585/607 |

*Primary Examiner*—Jacqueline V. Howard
*Attorney, Agent, or Firm*—Wenderoth, Lind & Ponack

[57] ABSTRACT

A process for producing isoprene, which comprises decomposing a mixture of at least two compounds represented by the general formula

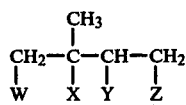

wherein (i) W and Y each represent a hydrogen atom, and X and Z are identical or different and each represent the group OR, (ii) W and X together form a single bond, Y represents a hydrogen atom and Z represents the group OR, (iii) W represents a hydrogen atom, X and Y together form a single bond, and Z represents the group OR, or (iv) W represents a hydrogen atom, X represents the group OR, and Y and Z together form a single bond, in which R represents a hydrogen atom, a methyl group, a methoxymethyl group, a methylbutenyl group, a methylbutenyloxymethyl group, a 1,1-dimethyl-3-hydroxypropyl group, a 1,1-dimethyl-3-hydroxypropyloxymethyl group, a 3-methyl-3-hydroxybutyl group, a 3-methyl-3-hydroxybutyloxymethyl group, a 1,1-dimethyl-3-methoxypropyl group, a 1,1-dimethyl-3-methoxypropyloxymethyl group, a 3-methyl-3-methoxybutyl group or a 3-methyl-3-methoxybutyloxymethyl group, at least one compound of the mixture being a compound of general formula (I) in which R is a methoxymethyl group, a methylbutenyloxymethyl group, a 1,1-dimethyl-3-hydroxypropyloxymethyl group, a 3-methyl-3-hydroxybutyloxymethyl group, a 1,1-dimethyl-3-methoxypropyloxymethyl group or a 3-methyl-3-methoxybutyloxymethyl group, in the presence of water and an oxygen-containing boron compound selected from the group consisting of boron-oxyacids and boron compounds capable of generating the boron-oxyacids in situ under the reaction conditions, in the liquid phase at a temperature of at least 150° C. while adjusting the ratio of the oxygen-containing boron compound to the entire water present in the reaction system such that the weight ratio of ortho-boric acid to water, calculated on the assumption that all the oxygen-containing boron compound changes in aqueous solution to orthoboric acid, is at least maintained at 15:85.

14 Claims, No Drawings

PROCESS FOR PRODUCING ISOPRENE

This invention relates to a novel process for producing isoprene, and more specifically, to a process for producing isoprene in a good yield by catalytically decomposing a mixture of at least two compounds selected from certain methylbutane derivatives and methylbutene derivatives.

The reaction of forming a double bond by decomposing an aliphatic alcohol, ether or acetal is carried out by a gas-phase method or a liquid-phase method. Generally, the gas-phase reaction is carried out at a relatively high temperature using a solid acid as a catalyst, and the liquid-phase reaction is carried out at a relatively low temperature using a strongly acidic substance as a catalyst. The reaction of forming a double bond by eliminating water, an alcohol, and a carbonyl compound from the aliphatic alcohol, ether or acetal gives very different results depending upon the kind and chemical structure of the starting material and the chemical structure of the resulting olefinic compound. When the resulting olefinic compound is a tertiary olefin or diene having high reactivity under acidic conditions, or when the alcohol or carbonyl compound eliminated during the reaction has high reactivity under acidic conditions, side-reactions tend to take place. Furthermore, because the activity of the catalyst is reduced during the reaction, it is difficult to perform the reaction in the gaseous phase or in the liquid phase over an extended period of time without activating or renewing the catalyst. According to prior techniques of the liquid-phase reaction, it is seen that the reaction proceeds under relatively mild conditions, and the apparatus and the operation of the reaction are simple. On the other hand, the liquid-phase reaction has the defect that the apparatus is corroded by the use of a strong acid such as sulfuric acid, phosphoric acid, a hydrohalic acid or a sulfonic acid as the catalyst and that the yields of the desired products decrease owing to the longer residence of the starting material and the products in the reaction system. Another defect of the liquid-phase reaction by the strong acid catalyst is that the catalyst should be renewed within a short period of time and that the waste catalyst must be neutralized before it is discarded.

It is an object of this invention to provide an industrially advantageous process for producing isoprene in a high yield by decomposing a readily available starting material in an aqueous solution of boron-oxyacids which are much weaker than the acids previously used for the dehydration reaction of aliphatic alcohols [for example, ortho-boric acid has a dissolution constant of only $5.8 \times 10^{-10}$ at 25° C.; see LANGE'S HANDBOOK OF CHEMISTRY, Page 1209, McGraw-Hill Book Co. (1967)].

According to this invention, there is provided a process for producing isoprene, which comprises decomposing a mixture of at least two compounds represented by the general formula

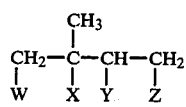

wherein (i) W and Y each represents a hydrogen atom, and X and Z are identical or different and each represents the group OR, (ii) W and X together form a single bond, Y represents a hydrogen atom and Z represents the group OR, (iii) W represents a hydrogen atom, X and Y together form a single bond, and Z represents the group OR, or (iv) W represents a hydrogen atom, X represents the group OR, and Y and Z together form a single bond, in which R represents a hydrogen atom, a methyl group, a methoxymethyl group, a methylbutenyl group, a methylbutenyloxymethyl group, a 1,1-dimethyl-3-hydroxypropyl group, a 1,1-dimethyl-3-hydroxypropyloxymethyl group, a 3-methyl-3-hydroxybutyl group, a 3-methyl-3-hydroxybutyloxymethyl group, 1,1-dimethyl-3-methoxypropyl group, a 1,1-dimethyl-3-methoxypropyloxymethyl group, a 3-methyl-3-methoxybutyl group or a 3-methyl-3-methoxybutyloxymethyl group, at least one compound of the mixture being a compound of general formula (I) in which R is a methoxymethyl group, a methylbutenyloxymethyl group, a 1,1-dimethyl-3-hydroxypropyloxymethyl group, a 3-methyl-3-hydroxybutyloxymethyl group, a 1,1-dimethyl-3-methoxypropyloxymethyl group or a 3-methyl-3-methoxybutyloxymethyl group, in the presence of water and an oxygen-containing boron compound selected from the group consisting of boron-oxyacids and boron compounds capable of generating the boron-oxyacids in situ under the reaction conditions, in the liquid phase at a temperature of at least 130° C. while adjusting the ratio of the oxygen-containing boron compound to the water present in the reaction system such that the weight ratio of the ortho-boric acid to water, on the assumption that all the oxygen-containing boron compound changes to ortho-boric acid in the aqueous solution, is maintained at 15:85 or higher.

The starting material used in the process of this invention for the production of isoprene is a mixture containing both at least one compound of general formula (I) in which R represents a hydrogen atom, a methyl group, a methylbutenyl group, a 1,1-dimethyl-3-hydroxypropyl group, a 3-methyl-3-hydroxybutyl group, a 1,1-dimethyl-3-methoxypropyl group or a 3-methyl-3-methoxybutyl group, and at least one compound of general formula (I) in which R represents a methyloxymethyl, methylbutenyloxymethyl, 1,1-dimethyl-3-hydroxypropyloxymethyl, 3-methyl-3-hydroxybutyloxymethyl, 1,1-dimethyl-3-methoxypropyloxymethyl or 3-methyl-3-methoxybutyloxymethyl group.

A compound in the former group (this compound may sometimes be referred to as "a formal linkage-free compound") sequentially or simultaneously undergoes decomposition of its ether linkage and/or elimination reaction of its hydroxyl group under the reaction conditions of the present invention and is converted to isoprene having a tertiary double bond with the simultaneous formation of water and/or methanol as by-products. A compound in the latter group is unique in that it has a formal linkage in the molecular (because of which this compound may sometimes be referred to as "a formal linkage-containing compound"). Thus, under the reaction conditions of the present invention, it undergoes decomposition of its ether linkage and/or elimination reaction of its hydroxyl group and also the cleavage of the formal linkage occurs. As a result, in addition to the formation of methanol and/or water as mentioned above, formaldehyde very reactive with a tertiary double bond is liberated together with isoprene.

The reactions which take place in the process of this invention are schematically shown below by taking up as an example a compound of general formula (I) in which W and Y are hydrogen atoms and X and Z are both hydroxyl groups [formula (I-1)] and a compound of general formula (I) in which both W and Y are hydrogen atoms, X is a methoxy group and Z is a 3-methyl-3-hydroxybutyloxymethyloxy group [formula (I-2)].

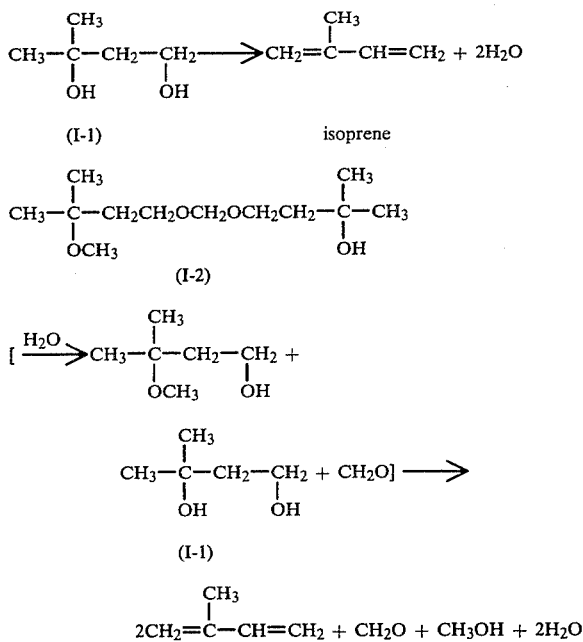

It is known that highly reactive isoprene is produced by the dehydration reaction of 3-methylbutane-1,3-diol having a primary and a tertiary hydroxyl group [the compound of formula (I-1)] and that it is difficult to obtain isoprene in a high yield since even pure 3-methylbutane-1,3-diol free from formal compounds and other impurities is liable to yield by-products such as ethers, carbonyl compounds and polymers. For example, Neftekkimiya 5, (3), 368–372 (1965) shows that when 3-methylbutane-1,3-diol is decomposed in a 0.5–10% by weight aqueous solution of sulfuric acid in the boiling state while distilling off the product, the yield of isoprene is only 66.5%. British Pat. No. 1,358,188 discloses that in the hydration reaction of 3-methylbutane-1,3-diol, 3-methyl-3-buten-1-ol or 2-methyl-3-buten-2-ol with an aqueous solution of an acid having a dissociation constant of $1 \times 10^{-6}$, isoprene can be obtained in an improved yield only in the presence of a halogen ion. These methods, however, have the defect that special care is required about the corrosion of the apparatus.

It is known that an olefin, especially a tertiary olefin, readily reacts with formaldehyde under acidic conditions to give various compounds [see Chem. Rev., 51 505 (1952)]. For example, Japanese Laid-Open Patent Publication No. 109906/79 discloses that when isobutene or isoamylene is reacted with formaldehyde in the presence of boric acid and water, an alkan-1,3-diol having 5 or 6 carbon atoms, respectively, is formed. It is also known that when 4-methyl-4-(β-methoxymethyloxy)ethyl-1,3-dioxane having linear and cyclic formal linkages is decomposed in the presence of boric acid and water, 3-methylpentane-1,3,5-triol having primary and tertiary hydroxyl groups which has a similar chemical structure to the above compound of formula (I-1) is obtained in good yields, but that olefins and olefinic alcohols, the dehydration products of the triol, scarcely form (see Japanese Laid-Open Patent Publication No. 62915/75 and U.S. Pat. No. 4,069,261).

When according to the process of this invention, a mixture of the compounds of general formula (I) is heated in the presence of water and a boron-oxyacid or a boron compound capable of forming the boron-oxyacid in situ under the reaction conditions, it has been found that isoprene, a tertiary diene, forms in a high yield with little consecutive side-reactions with the formaldehyde generated from the formal linkage-containing compounds of general formula (I). This fact is quite unexpected from the disclosures of the above-cited prior art references.

As stated hereinabove, the starting material for the production of isoprene in the process of this invention is a mixture of at least one compound of general formula (I) in which R represents a hydrogen atom or a methyl, methylbutenyl, 1,1-dimethyl-3-hydroxypropyl, 3-methyl-3-hydroxylbutyl, 1,1-dimethyl-3-methoxyropyl or 3-methyl-3-methoxybutyl group and at least one compound of general formula (I) in which R is a methoxymethyl, methylbutenyloxymethyl, 1,1-dimethyl-3-hydroxypropyloxymethyl, 3-methyl-3-hydroxybutyloxymethyl, 1,1-dimethyl-3-methoxypropyloxymethyl or 3-methyl-3-methoxybutyloxymethyl group.

Specific examples of the compounds in the former group (formal linkage-free compounds) include 3-methyl-3-buten-1-ol, 3-methyl-2-buten-1-ol, 2-methyl-3-buten-2-ol, 2-methyl-4-methoxy-1-butene, 2-methyl-4-methoxy-2-butene, 3-methyl-3-methoxy-1-butene, 3-methyl-1,3-dimethoxybutane, 3-methyl-3-methoxybutan-1-ol, 1-methoxy-3-methylbutan-3-ol, 3-methylbutan-1,3-diol, 3-(3-methyl-3-methoxybutyloxy)-3,3-dimethylpropan-1-ol, 3-(3-methyl-3-hydroxybutyloxy)-3,3-dimethylpropan-1-ol, 3-(3-methyl-3-butenyloxy)-3,3-dimethylpropan-1-ol, 3-(3-methyl-2-butenyloxy)-3,3-dimethylpropan-1-ol, 1-(3-methyl-2-butenyloxy)-3-methyl-3-methoxybutane, 1-(3-methyl-2-butenyloxy)-3-methyl-3-hydroxybutane, 1-(3-methyl-2-butenyloxy)-3-methyl-3-butene, 1-(3-methyl-2-butenyloxy)-3-methyl-2-butene, 1-(1,1-dimethyl-2-propenyloxy)-3-methyl-3-methoxybutane, 1-(1,1-dimethyl-2-propenyloxy)-3-methyl-3-hydroxybutane, 1-(1,1-dimethyl-2-propenyloxy)-3-methyl-3-butene and 1-(1,1-dimethyl-2-propenyloxy)-3-methyl-2-butene.

Specific examples of the compounds in the latter group (formal linkage-containing compounds) include 3-methyl-3-methoxybutyl methyl formal, 1,1-dimethyl-3-methoxypropyl methyl formal, 3-methyl-3-hydroxybutyl methyl formal, 1,1-dimethyl-3-hydroxypropyl-methyl formal, 3-methyl-3-butenyl methyl formal, 3-methyl-2-butenyl methyl formal, bis(3-methyl-3-methoxybutyl)formal, bis(3-methyl-3-hydroxybutyl)formal, 3-methyl-3-methoxybutyl 3'-methyl-3'-hydroxybutyl formal, 3-methyl-3-butenyl 3'-methyl-3'-methoxybutyl formal, 3-methyl-2-butenyl 3'-methyl-3'-methoxybutyl formal, bis(3-methyl-3-butenyl)formal, bis(3-methyl-2-butenyl)formal, 3-methyl-3-butenyl 3'-methyl-2'-butenyl formal, 3-(3-methyl-3-methoxybutyloxy)-3,3-dimethylpropyl methyl formal, 3-(3-methyl-3-hydroxybutyloxy)-3,3-dimethylpropyl methyl formal, 3-(3-methyl-3-butenyloxy)-3,3-dimethylpropyl methyl formal, 3-(3-methyl-2-butenyloxy)-3,3-dimethylpropyl methyl formal, 1,1-dimethyl-3-hydroxypropyl 3'-methyl-3'-methoxybutyl formal, 1,1-dimethyl-3-hydroxypropyl, 3'-methyl-3'-hydroxybutyl formal, 1,1-dimethyl-3-hydroxypropyl 3'-methyl-3'-butenyl formal, 1,1- dimethyl-3-hydroxypropyl 3'-methyl-2'-butenyl formal, 1,1-dimethyl-3-(3-methyl-2-butenyloxy)-propyl methyl formal and 1,1-dimethyl-3-(1,1-dimethyl-3-hydroxypropyloxy)-propyl methyl formal.

The starting material used in the process of this invention may be a mixture of any two or more compounds of general formula (I) provided that at least one of them is the formal linkage-containing compound in the latter group. The composition of the mixture and the proportions of the constituent ingredients are not critical. However, the use of a large proportion of the formal linkage-containing compound in the starting mixture results in a low yield of isoprene owing to the increase of undesirable side-reactions. Desirably, therefore, the total amount of the formal linkage-containing compounds in the starting mixture is generally limited to at most 50% by weight, and an industrially obtainable starting mixture usually contains 40–95% by weight of the formal linkage-free compounds and 5–50% by weight of the formal linkage-containing compounds of general formula (I), based on the total weight of the starting mixture.

The starting material used in the process of this invention may further include a small amount (usually up to about 10% by weight based on the weight of the starting material) of one or more compounds such as 4,4-dimethyl-1,3-dioxane, isobutylene, tertiary butylalcohol, methanol, methyl t-butyl ether, 3-methyl-3-methoxybutyl t-butyl formal, 3-methyl-3-hydroxybutyl t-butyl formal, 3-methyl-3-butenyl t-butyl formal and 3-methyl-2-butenyl t-butyl formal.

A preferred starting material used in the process of this invention is a crude reaction product which is easily obtained industrially by methanolysis in the presence of an acid catalyst of 4,4-dimethyl-1,3-dioxane formed by Prins reaction between isobutene and formaldehyde (for example, see Japanese Laid-Open Patent Publications Nos. 124205/78 and 12307/79).

When the compound of general formula (I) in the starting mixture has one or more hydroxyl groups, the hydroxyl groups may form an ester with a boron-oxyacid or its half ester.

Thus, according to a preferred embodiment in the process of this invention, there is provided a process for producing isoprene which comprises the steps, in combination of (1) subjecting isobutene and formaldehyde to Prins reaction to form 4,4-dimethyl-1,3-dioxane (first step), (2) methanolyzing the resulting 4,4-dimethyl-1,3-dioxane in the presence of an acid catalyst to obtain a product containing one or more compounds of general formula (I) given hereinabove (second step), and (3) subjecting the reaction product to the process of this invention to produce isoprene (third step).

The first and second steps of the above process are described in detail in the specifications of Japanese Laid-Open Patent Publication Nos. 124205/78 and 12307/79, and these patent documents have been cited herein in lieu of a detailed description of these steps.

Examples of the boron-oxyacid used as a catalyst in converting the aforesaid starting material into isoprene include orthoboric acid, metaboric acid, tetraboric acid and other condensed boric acids, and orthoboric acid is especially preferred in view of its availability. Examples of the oxygen-containing boron compound include boric anhydride, esters formed between boric acid and lower aliphatic alcohols having 1 to 6 carbon atoms (such as methanol, ethanol, iso-propanol, tertiary butanol, 3-methyl-3-buten-1-ol, 3-methyl-3-methoxybutan-1-ol and 3-methylbutan-1,3-diol). Tertiary butyl borate is especially preferred. These oxygen-containing boron compounds may be used singly or as a mixture of two or more.

In practising the process of this invention, the oxygen-containing boron compound must be used together with water. Water is used in such an amount that the weight ratio of orthoboric acid to water, calculated on the assumption that all the oxygen-containing boron compound changes in aqueous solution to orthoboric acid, is at least 15:85. When the above weight ratio does not reach 15:85, the reaction cannot proceed practically. There is no upper limit to the above weight ratio, and orthoboric acid may be present in an amount exceeding its solubility under the reaction conditions. When orthoboric acid is present in the reaction system in an amount exceeding its solubility in water under the reaction conditions, the undissolved portion of the orthoboric acid naturally disperses as a fine powder. This, however, does not specially hamper the practice of the present invention. In practice, the oxygen-containing boron compound and water are advantageously used in proportions not exceeding the solubility of boron-oxyacid under the reaction conditions, and preferably used in such proportions that the aforesaid weight ratio of orthoboric acid to water is from 30:70 to 60:40, more preferably from 40:50 to 50:50.

In the reaction system of this invention, the use of the oxygen-containing boron compounds in a high concentration brings about incidental effects of reducing the amount of organic materials dissolved in the aqueous solution of the boron-oxyacid and at the same time increasing the separability of the organic materials from the aqueous solution. Consequently, consecutive side-reactions of the product in the reaction zone can be inhibited, and high-boiling by-products accumulated during a long period of the reaction are easy to separate and remove from the reaction zone.

The reaction of this invention is carried out at a temperature of at least 130° C. If the reaction temperature is less than 130° C., a substantial reaction rate cannot be obtained, and the yield of isoprene is drastically reduced. In view of the reaction pressure, the suitable temperature is not more than 250° C., and the preferred temperature is in the range of 150° C. to 230° C. The reaction temperature is generally selected from the above-specified range according to the concentration of the boron-oxyacid in the aqueous medium under the reaction conditions. Usually, lower temperature is preferred when the concentration is higher, and conversely, higher temperature is preferred when the concentration is lower.

Since the reaction needs to be carried out in the liquid phase at the above reaction temperature, it is usually carried out at elevated pressures. It is preferred to exert such a pressure at which the liquid phase boils under the reaction conditions. Generally, the pressure may be the autogeneous pressure of the boiling reaction system. By maintaining the liquid phase in the boiling state, it is easy to distill off the reaction products together with water.

The concentration of the starting material in the aqueous solution of boron-oxyacids is not critical, but usually the suitable concentration is not more than 10% by weight, preferably not more than 5% by weight. If the concentration of the starting mixture is too high, the amount of high-boiling by-products increases so that the by-products build up in the reaction system, causing the decrease of the reaction rate.

The aqueous solution of the oxygen-containing boron compounds in which high-boiling by-products has built up as a result of the performance of the process of this invention, if necessary, is taken out from the reaction system either wholly or partly, and purified by known means such as decantation, extraction, concentration or recrystallization. If desired, the boron-oxyacid is recovered for reuse. Since the separability of the high-boiling by-products accumulated in the reaction system from the aqueous solution is good in the process of this invention using an aqueous solution of boron-oxyacids in a high concentration, the decantation method is preferred in removing these by-products.

The process of this invention may be carried out non-continuously, but it is advantageous to carry it out continuously. A method involving stripping off continuously the reaction product containing isoprene as a major component out of the reaction system with water is effective for inhibiting side-reactions and increasing the yield of isoprene. Hence, the continuous operation is recommendable.

An especially preferred example of the continuous operation is a method which comprises continuously introducing a mixture of two or more of the compounds of general formula (I) into an aqueous solution of the boron-oxyacid with stirring at a given temperature and pressure and simultaneously stripping off the product continuously out of the reaction system with water. The stripped vapor is condensed, and the lower layer (aqueous layer) may be wholly or partly recycled to the reaction system. In this method, it is possible to feed the starting material with a certain proportion of water or steam and take out the reaction product together with the excess of water in the reaction system. Since the aqueous layer obtained from the condensate contains the starting material or an isoprene intermediate dissolved therein, recycling of a part or the whole of it to the reactio system contributes to the increasing of the yield of isoprene and to the decreasing of the amount of waste water discharged, and is especially advantageous in industrial practice. The suitable amount of water or steam fed to the reaction system is preferably 0.5 to 5 parts by weight, more preferably 1 to 4 parts by weight, per part by weight of the starting material. No particular inconvenience is caused even when the amount of water or steam fed exceeds the specified upper limit. It is disadvantageous only in that the amount of waste water increases.

In the process of this invention, one or more solvents or diluents inert to the reaction may also be used together with water. Such a solvent or diluent should be a volatile liquid organic compound which boils under the reaction conditions. Examples include aliphatic, alicyclic and aromatic hydrocarbons such as benzin fraction, hexane, cyclohexane, methylcyclohexane, benzene, toluene and xylene.

When the reaction is carried out over a long period of time, small amounts of high-boiling by-products, especially tarry by-products, build up in the reaction system. Because the specific gravity of these by-products is much lower than that of the aqueous solution of the boric acids in the reaction system, they can be easily removed by transferring a part of the boric acid-water mixture containing these high-boiling by-products to a decanter. The boric acid-water mixture from which the high-boiling by-products have thus been removed is recycled to the reaction system. Accordingly, the aqueous solution of a boron-oxyacid which functions both as a catalyst and a solvent for performing the reaction in the liquid phase can be repeatedly used over a long period of time without being subjected to any special regeneration or purification step.

The aqueous solution of boron-oxyacid used as a catalyst in the process of this invention is very advantageous in industrial practice over other inorganic acids in that it does not corrode the reaction apparatus. According to the investigations of the present inventors, SUS27 stainless steel and SUS36 stainless steel scarcely undergo a weight decrease in a 60% by weight aqueous solution of ortho-boric acid maintained at 190° C. in a nitrogen atmosphere as shown in Table A below, and thus it is clear that the aqueous solution of boric acid in a concentration of 60% by weight does not corrode SUS27 and SUS36 stainless steel at 190° C.

TABLE A

| Time (hours) | Weight decrease (% by weight) | | | | |
| --- | --- | --- | --- | --- | --- |
|  | 6 | 12 | 18 | 24 | 30 |
| SUS27 stainless steel (surface area 32.7 cm$^2$) | 0.004 | 0.020 | 0.020 | 0.020 | 0.020 |
| SUS36 stainless steel (surface area 36.7 cm$^2$) | 0.166 | 0.180 | 0.182 | 0.186 | 0.186 |

Isoprene obtained by the process of this invention is a very important compound in polymer industry as raw materials for production of synthetic rubbers, terpene compounds, etc. and in chemical industry dealing with perfumes, medicines and agricultural chemicals.

The following Examples illustrate the present invention more specifically. It should be understood that the invention is in no way limited by these examples.

EXAMPLE 1

A pressure glass reaction apparatus consisting of a reactor (500 ml) adpated for electromagnetic stirrer and equipped with a material-introducing tube, a thermometer, and a distillate receiver connected to a condenser was charged with 90 g of ortho-boric acid and 210 g of water, and with stirring, they were heated and maintained at 180° C. A 25% by weight aqueous solution of a starting material having the composition shown in Table 1 below was introduced into the reaction system maintained in the above condition through the material-introducing tube at a rate of 180 g/hr, and was reacted. Simultaneously with the introduction of the starting material, isoprene formed, and the reaction system boiled. The resulting isoprene was distilled off together with water, condensed by the condenser, and trapped in the receiver. After the aqueous solution was fed for a total period of 2 hours, water alone was introduced at the same rate for 5 minutes. Then, the reaction was stopped. During the reaction, the pressure of the reaction system was maintained at 8.5 kg/cm$^2$.G, and the amount of the liquid in the reaction system was maintained almost constant. The distillate trapped in the receiver was separated into an organic layer and an aqueous layer, and the organic layer was analyzed by gas chromatography. The aqueous layer was treated with an alkali and the dissolved organic materials were extracted with diethyl ether by a continuous extractor. The extract was subjected to the above analysis. In the meantime, the aqueous solution of boric acid in the reactor was cooled to precipitate boric acid which was recovered by filtration. The filtrate was analyzed in the same way as in the analysis of the aqueous layer of the distillate. The following results were calculated on the assumption that one molecule of isoprene formed from one molecule each of the components (3) to (9) shown in Table 1 and two molecules of isoprene formed from one molecule each of the components (10) to (13) shown in Table 1, and isoprene did not form from the component (2).

| | |
|---|---|
| Conversion | 98.8% |
| Selectivity for | |
| Isoprene | 86.7% |
| 3-Methyl-3-buten-1-ol | 4.5% |
| 3-Methyl-2-buten-1-ol | 0.5% |
| 2-Methyl-3-buten-2-ol | 2.7% |

The 3-methyl-3-buten-1-ol and other methylbutenyl alcohols are compounds expressed by general formula (I) as starting materials in this invention.

TABLE 1

| Components | Proportions |
|---|---|
| (1) Water | 6.26% |
| (2) Low-boiling compounds* | 3.32 |
| (3) 3-Methyl-1,3-dimethoxybutane | 0.59 |
| (4) 4,4-Dimethyl-1,3-dioxane | 0.82 |
| (5) 3-Methyl-3-buten-1-ol | 0.27 |
| (6) 3-Methyl-2-methoxybutyl methyl formal | 2.56 |
| (7) 3-Methyl-3-methoxybutan-1-ol | 13.8 |
| (8) 3-Methyl-3-hydroxybutyl methyl formal | 0.46 |
| (9) 3-Methylbutane-1,3-diol | 64.9 |
| (10) 3-(3-Methyl-3-methoxybutyloxy)-3,3-dimethylpropan-1-ol | 1.42 |
| (11) 1,1-Dimethyl-3-hydroxypropyl 3'-methyl-3'-methoxybutyl formal | 2.66 |
| (12) 3-(3-Methyl-3-hydroxybutyloxy)-3,3-dimethylpropan-1-ol | 1.64 |
| (13) 3-(3-Methyl-3-hydroxybutyloxy)-3,3-dimethylpropyl methyl formal | 1.29 |

*Methylal, 3-methylbutanal, 2-methylbutanal, 3-methyl-2-butanone, etc.

EXAMPLE 2

A pressure glass reaction apparatus was used which consisted of a 500 ml reactor equipped with a starting material introducing tube, a recycled aqueous solution introducing tube, a thermometer, a condenser, an electromagnetic stirrer and two distillate receivers connected by a three-way cock and being adapted to recycle the distilled aqueous layer to the reactor from the bottoms of the two receivers by means of a pressure metering pump. The reactor was charged with 135 g of orthoboric acid and 165 g of water and they were heated and dissolved. The resulting aqueous solution was maintained at 170° C., and with stirring, a 62.5% aqueous solution of the same starting material as shown in Table 1 was introduced into the reactor at a rate of 172.8 g/hr by the pressure metering pump, and reacted. Simultaneously with the introduction of the starting material, isoprene formed, and the reaction system boiled. The resulting isoprene was distilled out from the reaction system together with steam, condensed by the condenser, and trapped in the receiver. During this time, the aqueous layer forming the under layer in the receiver was recycled to the reactor at a rate of 172.8 g/hr by the pressure metering pump. During the reaction, the pressure was constant at 5.6 kg/cm$^2$.G. The amount of the liquid in the reaction system was maintained almost constant. Starting six hours after the initiation of the reaction, the distillate was trapped in the second receiver for two hours, and the distillate was treated and analyzed by the same operation as in Example 1. The reaction results were calculated in the same way as in Example 1.

| | |
|---|---|
| Conversion | 98.5% |
| Selectivity for | |
| Isoprene | 87.6% |
| 3-Methyl-3-buten-1-ol | 1.8% |
| 3-Methyl-2-buten-1-ol | 0.2% |
| 2-Methyl-3-buten-2-ol | 1.3% |

EXAMPLE 3

The same operation as in Example 2 was performed continuously for 147 hours in the same apparatus and under the same conditions as in Example 2 except that a starting material of the composition shown in Table 2 was used. The recycle ratio of the distilled aqueous solution [(recycled aqueous solution)/(recycled aqueous solution+freshly supplied water)] was adjusted to 0.80.

TABLE 2

| Components | Proportions |
|---|---|
| (1) Water | 5.50% |
| (2) Low-boiling compounds | 0.44 |
| (3) 3-Methyl-1,3-dimethoxybutane | 1.03 |
| (4) 4,4-Dimethyl-1,3-dioxane | 1.38 |
| (5) 3-Methyl-3-buten-1-ol | 0.12 |
| (6) 3-Methyl-2-buten-1-ol | 0.10 |
| (7) 3-Methyl-3-methoxybutyl methyl formal | 2.14 |
| (8) 3-Methyl-3-methoxybutan-1-ol | 9.73 |
| (9) 3-Methyl-3-hydroxybutyl methyl formal | 0.59 |
| (10) 3-Methylbutan-1,3-diol | 70.1 |
| (11) 3-(3-Methyl-3-methoxybutyloxy)-3,3-dimethylpropan-1-ol | 2.32 |
| (12) 1,1-Dimethyl-3-hydroxypropyl 3'-methyl-3'-methoxybutyl formal | 3.24 |
| (13) 3-(3-Methyl-3-hydroxybutyloxy)-3,3-dimethylpropyl methyl formal | 1.33 |
| (14) 3-(3-Methyl-3-hydroxybutyloxy)-3,3-dimethylpropan-1-ol | 2.00 |

The selectivities for the products are shown in Table 3. These values were measured on the assumption that one molecule of isoprene formed from one molecule each of the components (3) to (10) and two molecules of isoprene formed from one molecule each of the components (11) to (14), and the conversion was 100%.

TABLE 3

| Time (hours) | 3–5 | 58–60 | 94–96 | 145–147 |
|---|---|---|---|---|
| Isoprene | 87.1% | 87.1% | 87.0% | 86.7% |
| 3-Methyl-3-buten-1-ol | 1.17 | 1.23 | 1.29 | 1.99 |
| 3-Methyl-2-buten-1-ol | 0.13 | 0.09 | 0.04 | 0.14 |
| 2-Methyl-3-buten-2-ol | 1.24 | 1.29 | 1.33 | 1.37 |

The amount of tarry products accumulated in the reactor at the end of the reaction was 0.41% by weight based on the total amount of the material fed, and 19% by weight based on the boric acid-water mixture in the reactor. When the stirring of the reaction mixture was stopped at the reaction temperature, the tarry products separated within 25 seconds, and can be withdrawn easily by decantation.

EXAMPLE 4

A starting material of the composition shown in Table 4 was fed at a rate of 154 g/hr and fresh water was fed at a rate of 170 g/hr without recycling the distilled aqueous solution. Otherwise, the same operation as in Example 2 was repeated. The results are shown below. The reaction results were determined on the assumption that the component (7) also decomposed to give two molecules of isoprene under the reaction conditions.

| | |
|---|---|
| Conversion | 99.4% |
| Selectivity for | |
| Isoprene | 80.8% |
| 3-Methyl-3-buten-1-ol | 1.5% |
| 3-Methyl-2-buten-1-ol | 0.1% |
| 2-Methyl-3-buten-2-ol | 1.7% |

TABLE 4

| | Components | Proportions |
|---|---|---|
| (1) | 3-Methyl-1,3-dimethoxybutane | 3.56% |
| (2) | 4,4-Dimethyl-1,3-dioxane | 1.31 |
| (3) | 2-Methyl-4-methoxybutan-2-ol | 3.40 |
| (4) | 3-Methyl-3-methoxybutyl methyl formal | 20.9 |
| (5) | 3-Methyl-3-methoxybutan-1-ol | 63.2 |
| (6) | 3-Methylbutan-1,3-diol | 4.95 |
| (7) | Isoprene dimers | 2.55 |

EXAMPLES 5 TO 7

A starting mixture having the same composition as in Table 2 was reacted under the conditions shown in Table 5 in the same reaction apparatus as used in Example 2. Otherwise, the same operation as in Example 4 was repeated. The results are also shown in Table 5.

EXAMPLES 8 AND 9

Each of the same starting mixture as shown in Tables 1 and 2 was reacted under the conditions shown in Table 5. Otherwise, the same operation as in Example 4 was repeated. The results are also shown in Table 5.

EXAMPLE 10

The same starting mixture as shown in Table 2 was reacted in the same way as in Example 2 except that the weight ratio of the feed aqueous solution (fresh water + recycle aqueous solution) to the starting mixture was adjusted to 2.0, and the rate of recycling the distilled aqueous solution was adjusted to 129.6 g/hr. The results are shown in Table 5.

EXAMPLE 11

The same reaction as in Example 9 was performed except that the amount of ortho-boric acid and water charged were changed to 45 g and 255 g, respectively, and the reaction temperature was changed to 200° C. The results are also shown in Table 5.

TABLE 5

| | | Example | | | | | | |
|---|---|---|---|---|---|---|---|---|
| | | 5 | 6 | 7 | 8 | 9 | 10 | 11 |
| Composition of ortho-boric acid and water charged (g of boric acid/g of water) | | 120/180 | 135/165 | 120/180 | 120/180 | 60/240 | 135/165 | 45/255 |
| Reaction temperature (°C.) | | 170 | 170 | 180 | 180 | 180 | 170 | 200 |
| Rate of feeding the material (g/hr) | | 108 | 108 | 144 | 108 | 36 | 108 | 36 |
| Rate of feeding fresh water (g/hr) | | 0 | 0 | 0 | 216 | 144 | 86.4 | 144 |
| Rate of feeding recycle aqueous solution (g/hr) | | 216 | 162 | 288 | 0 | 0 | 129.6 | 0 |
| Reaction pressure (kg/cm².G) | | 5.9 | 5.7 | 8.0 | 8.0 | 9.8 | 5.6 | 13.8 |
| Conversion (%) | | 99.0 | 99.3 | 99.1 | 99.2 | 97.1 | 99.3 | 97.4 |
| Selectivity (%) | Isoprene | 85.3 | 86.8 | 84.7 | 88.4 | 71.8 | 88.3 | 66.6 |
| | 3-Methyl-3-buten-1-ol | 2.3 | 0.6 | 1.6 | 1.5 | 14.7 | 2.1 | 20.3 |
| | 3-Methyl-2-buten-1-ol | 0.2 | 0.2 | 0.4 | 0.5 | 0.7 | 0.3 | 1.4 |
| | 2-Methyl-3-buten-1-ol | 1.1 | 0.9 | 0.7 | 1.4 | 6.1 | 1.3 | 6.4 |

COMPARATIVE EXAMPLE 1

The reaction of Example 4 described in British Pat. No. 1,358,188 was carried out in accordance with the process of this invention.

A 200 ml four-necked flask equipped with a stirrer, a thermometer, a material-feeding tube, a condenser, and a receiver connected to a trap containing an absorbent (diisopropyl ether) cooled with a dry ice/acetone cooling medium bath, was charged with 71.44 g of water, 4.76 g of 85% phosphoric acid and 23.81 g of sodium bromide. With stirring, these materials were heated to boiling. The same starting material as used in Example 1 and water were introduced at a rate of 360 g/hr and 720 g/hr, respectively, into the resulting solution; the reaction was performed while distilling off the formed isoprene together with water out of the reaction system in the same way as in Example 1; and two hours later, the introduction of the starting material was stopped and water alone was introduced at the same rate for 5 minutes.

For comparison, the above reaction was repeated except that a 40% by weight aqueous solution of boric acid was used as the aqueous solution of the catalyst and the reaction temperature was maintained at 170° C. (the process of this invention).

The results are shown in Table 6. It was found that when in the method described in British Pat. No. 1,358,188, the isoprene formed was distilled out in accordance with the process of this invention together with the water formed in the reaction and the water fed to the reaction system, the acid present in the reaction system distilled out of the reaction system in a corresponding amount. In the present Comparative Example, an amount of hydrobromic acid which corresponded to 55 mole% of sodium bromide added to the reaction system at the beginning of the reaction was detected from the distilled aqueous layer.

TABLE 6

| | Catalyst | Conversion (%) | Selectivity (%) | | |
|---|---|---|---|---|---|
| | | | Isoprene | 3-Methyl-3-buten-1-ol | 2-Methyl-3-buten-2-ol |
| Comparative Example 1 | Aqueous solution of phosphoric acid and sodium bromide | 94.4 | 39.4 | 14.3 | 20.6 |
| Process of this invention | Aqueous solution of boric acid | 99.1 | 88.4 | 1.48 | 1.35 |

COMPARATIVE EXAMPLES 2 AND 3

Examples 9 and 11 were repeated except that the amounts of ortho-boric acid and water were changed to 30 g and 270 g, respectively. The results are shown in Table 7.

TABLE 7

| Comparative Example | | 2 | 3 |
|---|---|---|---|
| Orthoboric acid-water composition charged (g of boric acid/g of water) | | 30/270 | 30/270 |
| Reaction temperature (°C.) | | 180 | 200 |
| Rate of feeding the starting material (g/hr) | | 36 | 36 |
| Rate of feeding fresh water (g/hr) | | 144 | 144 |
| Rate of feeding recycle aqueous solution (g/hr) | | 0 | 0 |
| Reaction pressure (kg/cm$^2$.G.) | | 9.5 | 14.1 |
| Conversion (%) | | 70.8 | 84.6 |
| Selectivity (%) | Isoprene | 23.5 | 35.4 |
| | 3-Methyl-3-buten-1-ol | 52.9 | 43.7 |
| | 3-Methyl-2-buten-1-ol | 3.4 | 3.2 |
| | 2-Methyl-3-buten-2-ol | 13.0 | 11.9 |

EXAMPLE 12

Boric anhydride (50.8 g) was used instead of 90 g of ortho-boric acid, and the amount of water was increased to 249.2 g. Otherwise, the starting material shown in Table 1 was reacted in the same way as in Example 1. The results were as follows:

| Conversion | 98.9% |
|---|---|
| Selectivity for | |
| Isoprene | 86.5% |
| 3-Methyl-3-buten-1-ol | 4.3% |
| 3-Methyl-2-buten-1-ol | 0.5% |
| 2-Methyl-3-buten-2-ol | 3.0% |

EXAMPLE 13

The apparatus described in Example 1 was charged with 230 g of methyl borate and 290 g of water, and the temperature was raised to 170° C. over the course of about 30 minutes with stirring while the pressure of the reaction system was being maintained at 5.6 kg/cm$^2$.G. During this period, 210 g of methanol and 8.6 g of water were distilled off. The starting material shown in Table 1 was reacted in the same way as in Example 1. The results were as follows:

| Conversion | 98.8% |
|---|---|
| Selectivity for | |
| Isoprene | 86.0% |
| 3-Methyl-3-buten-1-ol | 4.2% |
| 3-Methyl-2-buten-1-ol | 0.5% |
| 2-Methyl-3-buten-2-ol | 2.7% |

EXAMPLE 14

The apparatus described in Example 1 was charged with 150 g of ortho-boric acid and 150 g of water, and with stirring, they were heated to form a solution maintained at 175° C. Then, a starting material of the composition shown in Table 8 and water were introduced into the reaction system maintained in this state at a rate of 54 g/hr and 270 g/hr, respectively, by means of a pressure-resistant metering pump, and reacted. Isoprene distilled off together with water, and was condensed by the condenser and trapped by the receiver. After the material and water were introduced for a total period of 3 hours, water alone was introduced at the same rate for 5 minutes and the reaction was stopped. During the reaction, the pressure of the reaction system was maintained at 6.8 kg/cm$^2$.G, and the amount of the liquid in the reaction system was controlled to a constant level. The distillate trapped in the receiver and the aqueous boric acid solution in the reactor were treated and analyzed in the same way as in Example 1. The following reaction results were calculated on the assumption that one molecule of isoprene formed from one molecule of each of the components (1) to (4), and two molecules of isoprene formed from one molecule of each of the components (5) to (10).

| Conversion | 100% |
|---|---|
| Selectivity for | |
| Isoprene | 81.2% |
| 3-Methyl-3-buten-1-ol | 2.0% |
| 3-Methyl-2-buten-1-ol | 0.2% |
| 2-Methyl-3-buten-2-ol | 1.1% |

TABLE 8

| Components | Proportion (wt. %) |
|---|---|
| (1) 3-Methyl-butane-1,3-diol | 4.5 |
| (2) 3-Methyl-3-methoxybutan-1-ol | 2.7 |
| (3) 1-Methoxy-3-methylbutan-3-ol | 1.6 |
| (4) 3-Methyl-3-hydroxybutyl t-butyl formal | 1.2 |
| (5) 3-Methyl-3-butenyl 3-methyl-3-hydroxybutyl formal | 1.8 |
| (6) 3-(3-methyl-3-methoxybutyloxy)-3,3-dimethylpropan-1-ol | 3.3 |
| (7) 3-(3-Methyl-3-hydroxybutyloxy)-1,1-dimethylpropyl methyl formal | 3.2 |
| (8) 1,1-Dimethyl-3-hydroxypropyl-3-methyl-3-methoxybutyl formal | 9.8 |
| (9) 3-(3-methyl-3-hydroxybutyloxy)-3,3-dimethylpropan-1-ol | 45.7 |
| (10) 1,1-Dimethyl-3-hydroxypropyl-3-methyl-3-hydroxybutyl formal | 26.2 |

What we claim is:

1. A process for producing isoprene, which comprises decomposing a mixture of at least two compounds represented by the general formula

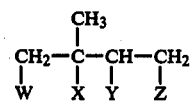  (I)

wherein (i) W and Y each represent a hydrogen atom, and X and Z are identical or different and each represent the group OR, (ii) W and X together form a single bond, Y represents a hydrogen atom and Z represents the group OR, (iii) W represents a hydrogen atom, X and Y together form a single bond, and Z represents the group OR, or (iv) W represents a hydrogen atom, X represents the group OR, and Y and Z together form a single bond, in which R represents a hydrogen atom, a methyl group, a methoxymethyl group, a methylbutenyl group, a methylbutenyloxymethyl group, a 1,1-dimethyl-3-hydroxypropyl group, a 1,1-dimethyl-3-hydroxypropyloxymethyl group, a 3-methyl-3-hydroxybutyl group, a 3-methyl-3-hydroxybutyloxymethyl group, a 1,1-dimethyl-3-methoxypropyl group, a 1,1-dimethyl-3-methoxypropyloxymethyl group, a 3-methyl-3-methoxybutyl group or a 3-methyl-3-methoxybutyloxymethyl group, and which contains both at least one formal linkage-free compound of general formula (I) in which R is a hydrogen atom, a methyl group, a methylbutenyl group, a 1,1-dimethyl-3-hydroxypropyl group, a 3-methyl-3-hydroxybutyl group, a 1,1-dimethyl-3-methoxypropyl group or a 3-methyl-3-methoxybutyl group and at least one formal linkage-containing compound of the general formula (I) in which R is a methoxymethyl group, a methylbutenyloxymethyl group, a 1,1-dimethyl-3-hydroxypropyloxymethyl group, a 3-methyl-3-hydroxybutyloxymethyl group, a 1,1-dimethyl-3-methoxypropyloxymethyl group or a 3-methyl-3-methoxybutyloxymethyl group, in the presence of water and an oxygen-containing boron compound selected from the group consisting of boron-oxyacids and boron compounds capable of generating the boron-oxyacids in situ, in the liquid phase at a temperature of at least 150° C. while adjusting the ratio of the oxygen-containing boron compound to the entire water present in the reaction system such that the weight ratio of orthoboric acid to water, calculated on the assumption that all the oxygen-containing boron compound changes in aqueous solution to orthoboric acid, is at least maintained at 15:85.

2. The process of claim 1 wherein said mixture contains at most 50% by weight, based on the weight of the mixture, of a compound of formula (I) in which R is a methoxymethyl, methylbutenyloxymethyl, 1,1-dimethyl-3-hydroxypropyloxymethyl, 3-methyl-3-hydroxybutyloxymethyl, 1,1-dimethyl-3-methoxypropyloxymethyl or 3-methyl-3-methoxybutyloxymethyl group.

3. The process of claim 1 wherein the mixture is a reaction product obtained by methanolizing 4,4-dimethyl-1,3-dioxane in the presence of an acid catalyst.

4. The process of claim 1 wherein the oxygen-containing boron compound is selected from the group consisting of orthoboric acid, metaboric acid, tetraboric acid, boric anhydride and esters formed between boric acid and lower aliphatic alcohols having 1 to 6 carbon atoms.

5. The process of claim 1 wherein the weight ratio of orthoboric acid to water is within the range of 40/60 to 50/50.

6. The process of claim 1 wherein the concentration of the mixture in the reaction system is at most 10% by weight based on the aqueous solution of boric acid.

7. The process of claim 6 wherein the concentration of the mixture in the reaction system is at most 5% by weight based on the aqueous solution of boric acid.

8. The process of claim 1 wherein the decomposition is carried out at a temperature of 150° to 230° C.

9. The process of claim 1 wherein the decomposition is carried out while continuously distilling off the reaction product containing isoprene as a major component out of the reaction system together with water.

10. The process of claim 9 wherein the decomposition is carried out while continuously feeding the starting mixture and water or steam into the reaction system and simultaneously distilling off continuously the reaction product containing isoprene as a major component out of the reaction system together with water.

11. The process of claim 10 wherein the amount of water or steam to be fed to the reaction system together with the starting mixture is 0.5 to 5 parts by weight per part by weight of the mixture.

12. The process of claim 10 wherein the distillate taken out of the reaction system is condensed, and the aqueous layer is recycled wholly or partly to the reaction system.

13. The process of claim 1 wherein the aqueous solution of a boron-oxyacid containing high-boiling compounds is withdrawn from the reaction system, the high-boiling compounds are separated from it, and then the remaining aqueous solution is recycled to the reaction system.

14. The process of claim 1 wherein the liquid phase of the reaction system is maintained in the boiling state.

* * * * *